United States Patent
Fourt et al.

(10) Patent No.: US 9,925,337 B2
(45) Date of Patent: Mar. 27, 2018

(54) DELAY MECHANISM SUITABLE FOR COMPACT AUTOMATIC INJECTION DEVICE

(71) Applicant: Eli Lilly and Company, Indianapolis, IN (US)

(72) Inventors: Jesse Arnold Fourt, Menlo Park, CA (US); Bradley James Simpson, Oakland, CA (US)

(73) Assignee: Eli Lilly and Company, Indianapolis, IN (US)

( * ) Notice: Subject to any disclaimer, the term of this patent is extended or adjusted under 35 U.S.C. 154(b) by 293 days.

(21) Appl. No.: 14/770,472

(22) PCT Filed: Mar. 7, 2014

(86) PCT No.: PCT/US2014/021485
§ 371 (c)(1),
(2) Date: Aug. 26, 2015

(87) PCT Pub. No.: WO2014/159017
PCT Pub. Date: Oct. 2, 2014

(65) Prior Publication Data
US 2016/0001004 A1    Jan. 7, 2016

Related U.S. Application Data

(60) Provisional application No. 61/783,007, filed on Mar. 14, 2013.

(51) Int. Cl.
*A61M 5/00* (2006.01)
*A61M 5/20* (2006.01)
*A61M 5/32* (2006.01)

(52) U.S. Cl.
CPC .......... *A61M 5/2033* (2013.01); *A61M 5/326* (2013.01); *A61M 5/3234* (2013.01); *A61M 2005/206* (2013.01)

(58) Field of Classification Search
CPC .......... A61M 2005/206; A61M 5/2033; A61M 5/326
See application file for complete search history.

(56) References Cited

U.S. PATENT DOCUMENTS 2,752,918 A    7/1956  Uytenbogaart
4,561,856 A    12/1985 Cochran
(Continued)

FOREIGN PATENT DOCUMENTS

EP    0470977    2/1992
EP    0653220    5/1995
(Continued)

OTHER PUBLICATIONS

Patent Cooperation Treaty International Search Report and Written Opinion of the International Searching Authority pertaining to International Application No. PCT/US2014/021485, dated May 20, 2014.

*Primary Examiner* — Kami A Bosworth
*Assistant Examiner* — William Carpenter
(74) *Attorney, Agent, or Firm* — M. Daniel Spillman

(57) ABSTRACT

A delay mechanism for an automatic injection device having a housing and a medication filled syringe. The delay mechanism includes a shuttle, a follower, a damping compound, at least one biasing member, and a biased plunger element. When moved in the device housing from a first location to a second location, the biased plunger element is adapted to drive the syringe piston within syringe barrel to force medication through the syringe needle for an injection. The follower, when the plunger element is so moved, is freed to move, under urging of the at least one biasing member, from a first position on the housing toward a second position to thereby move the shuttle for retracting the syringe needle into the housing after injection. The damping compound (Continued)

dampens or slows rotation of the follower as the follower moves from the first position toward the second position.

20 Claims, 18 Drawing Sheets

(56) References Cited

U.S. PATENT DOCUMENTS

| | | | |
|---|---|---|---|
| 4,744,786 A | 5/1988 | Hooven | |
| 4,893,805 A | 1/1990 | Eberle | |
| 5,080,649 A | 1/1992 | Vetter | |
| 5,150,933 A | 9/1992 | Myslicki et al. | |
| 5,167,304 A | 12/1992 | Capek | |
| 5,300,030 A | 4/1994 | Crossman et al. | |
| 5,346,480 A | 9/1994 | Hess et al. | |
| 5,393,301 A | 2/1995 | Goldberg | |
| 5,514,097 A * | 5/1996 | Knauer | A61M 5/20 604/136 |
| 5,540,664 A | 7/1996 | Wyrick | |
| 5,779,677 A | 7/1998 | Frezza | |
| 6,077,247 A | 6/2000 | Marshall et al. | |
| 6,159,181 A | 12/2000 | Crossman et al. | |
| 6,221,046 B1 | 4/2001 | Burroughs et al. | |
| 6,258,068 B1 | 7/2001 | Kirchhofer et al. | |
| 6,387,078 B1 | 5/2002 | Gillespie, III | |
| 6,454,743 B1 | 9/2002 | Weber | |
| 6,475,194 B2 | 11/2002 | Domici, Jr. et al. | |
| 6,544,234 B1 | 4/2003 | Gabriel | |
| 6,589,210 B1 | 7/2003 | Rolfe | |
| 6,632,198 B2 | 10/2003 | Caizza | |
| 7,066,907 B2 | 6/2006 | Crossman et al. | |
| 7,097,634 B2 | 8/2006 | Gilbert | |
| 7,361,160 B2 | 4/2008 | Hommann et al. | |
| 7,465,289 B2 | 12/2008 | Marshall | |
| 7,563,252 B2 | 7/2009 | Marshall et al. | |
| 7,635,356 B2 | 12/2009 | Stamp | |
| 7,699,816 B2 | 4/2010 | Kirchhofer et al. | |
| 7,758,548 B2 | 7/2010 | Gillespie et al. | |
| 7,901,377 B1 | 3/2011 | Harrison et al. | |
| 8,048,029 B2 | 11/2011 | Gillespie, III et al. | |
| 8,052,653 B2 | 11/2011 | Gratwohl et al. | |
| 8,167,840 B2 | 5/2012 | Matusch | |
| 8,734,394 B2 * | 5/2014 | Adams | A61M 5/2033 604/135 |
| 2003/0105430 A1 | 6/2003 | Lavi et al. | |
| 2004/0024367 A1 | 2/2004 | Gilbert | |
| 2006/0184132 A1 | 8/2006 | Watson | |
| 2006/0258990 A1 | 11/2006 | Weber | |
| 2007/0021720 A1 | 1/2007 | Guillermo | |
| 2007/0173770 A1 | 7/2007 | Stamp | |
| 2009/0012470 A1 | 1/2009 | Barrow-Williams | |
| 2010/0049125 A1 | 2/2010 | James et al. | |
| 2010/0069845 A1 | 3/2010 | Marshall et al. | |
| 2010/0160894 A1 | 6/2010 | Julian et al. | |
| 2011/0034878 A1 | 2/2011 | Radmer et al. | |
| 2012/0022466 A1 | 1/2012 | James et al. | |
| 2012/0323177 A1 * | 12/2012 | Adams | A61M 5/2033 604/135 |
| 2013/0123697 A1 | 5/2013 | Ekman et al. | |
| 2015/0246181 A1 * | 9/2015 | Fourt | A61M 5/2033 604/196 |
| 2016/0001004 A1 * | 1/2016 | Fourt | A61M 5/2033 604/198 |

FOREIGN PATENT DOCUMENTS

| | | |
|---|---|---|
| EP | 0678303 | 10/1995 |
| EP | 0996473 | 5/2000 |
| ES | 2070782 | 6/1995 |
| GB | 728248 | 4/1955 |
| GB | 2388033 | 11/2003 |
| GB | 2396298 | 6/2004 |
| GB | 2396816 | 7/2004 |
| GB | 2397767 | 8/2004 |
| GB | 2463034 | 3/2010 |
| WO | 9013325 | 11/1990 |
| WO | 9903529 | 1/1999 |
| WO | 00/24441 | 5/2000 |
| WO | 03/092771 | 11/2003 |
| WO | 03/097133 | 11/2003 |
| WO | 04/054645 | 7/2004 |
| WO | 2005/115508 | 12/2005 |
| WO | 2005/115512 | 12/2005 |
| WO | 2005/115514 | 12/2005 |
| WO | 2005/115516 | 12/2005 |
| WO | 2006/106291 | 10/2006 |
| WO | 2006/106295 | 10/2006 |
| WO | 2007/002052 | 1/2007 |
| WO | 2007/002053 | 1/2007 |
| WO | 2007/036676 | 4/2007 |
| WO | 2008/112472 | 9/2008 |
| WO | 2009/092807 | 7/2009 |
| WO | 2011109205 | 9/2011 |
| WO | 2014062488 | 4/2014 |

* cited by examiner

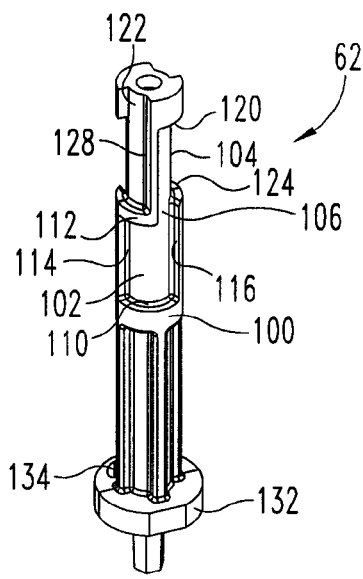
Fig. 13A
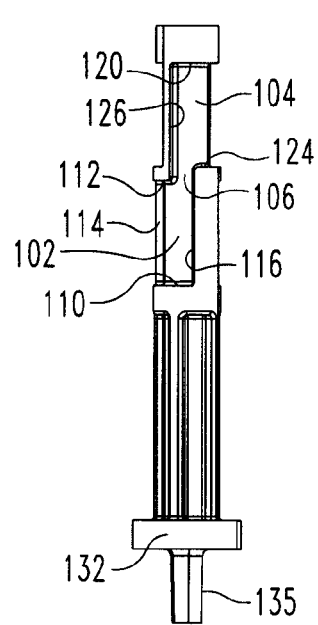 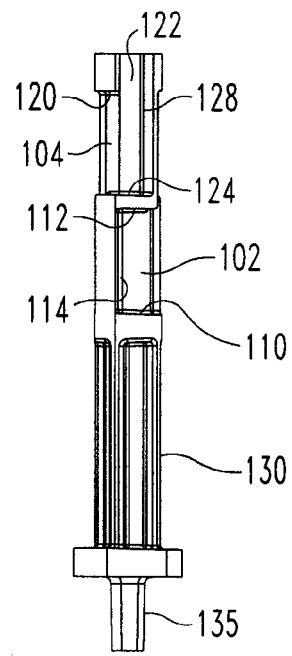
Fig. 13B         Fig. 13C

DELAY MECHANISM SUITABLE FOR COMPACT AUTOMATIC INJECTION DEVICE

PRIORITY

The present application claims the benefit and priority to and is a United States National Stage Entry of PCT/US2014/021485, filed 26 Aug. 2015, which claims priority to U.S. Provisional Application No. 61/783,007, filed on 14 Mar. 2013.

BACKGROUND OF THE INVENTION

The present invention pertains to pharmaceutical injection devices, and, in particular, to a mechanism used to delay needle retraction for an automatic injection device.

Patients suffering from a number of different diseases frequently must inject themselves with pharmaceuticals. A variety of devices have been proposed to facilitate these injections. One type of device is an automatic injection device. This type of device, when triggered by a user or someone helping the user, automatically inserts into the user a needle of a syringe that prior to triggering was disposed within the device housing, and then automatically injects a dose of medication through that inserted needle. One known type of automatic injection device then automatically advances a shroud to cover the needle when the dose is completed. In another type of automatic injection device having a configuration more desirable to some, and instead of having an advancing shroud, the device will automatically retract the needle into the housing when the dose is completed. To ensure that the full desired contents of the syringe have been injected prior to the syringe being retracted, a variety of differently configured delay mechanisms have been proposed for such automatic injection devices.

One problem with at least some automatic injection devices having delay mechanisms is that the devices are longer than some users may like when placed by the user on an injection site. All things being equal, a shorter device for a given delivery volume may be provided by making the syringe shorter but with a larger diameter. However, as causing such syringes to inject tends to require the application of more force and therefore a more robust drive system, constraints can result as to where the delay mechanism can be accommodated within the device housing. Still further, some delay mechanisms are not as compact axially as would be desirable to allow for the injection devices in which they are used to be short or compact.

Another problem with at least some automatic injection devices having delay mechanisms is that the means for holding the needle in a retracted position after use is less reliable than desired. It is possible with such devices for the needle to be released accidentally from a locked position after use despite the device experiencing a relatively minor impact or external force.

Thus, it would be desirable to provide an automatic injection device that can overcome one or more of these and other shortcomings of the prior art.

BRIEF SUMMARY OF THE INVENTION

In one form thereof, the present invention provides a delay mechanism for an automatic injection device having a housing and a medication filled syringe having a barrel, a piston, and an injection needle, the device being operable for moving the syringe in a first direction relative to the housing to extend the injection needle beyond the housing. The delay mechanism includes a shuttle, a follower, a damping compound, at least one biasing member, and a biased plunger element. The shuttle is rotatably fixed relative to the housing and configured for engaging the syringe for retraction. The follower is adapted for shifting the shuttle in a direction opposite to the first direction. The follower is keyed with the housing for movement from a first position on the housing to a second position on the housing, the second position being axially spaced from the first position in the direction opposite to the first direction, the second position being rotationally spaced from the first position. The damping compound is between surfaces of the follower and at least one of the shuttle and the housing to dampen rotation of said follower. The at least one biasing member provides a force urging the follower from the first position to the second position. The biased plunger element is adapted to drive the piston within the barrel to force medication through the injection needle for an injection. The biased plunger element is biased in the first direction within the housing from a first location to a second location, and is rotatably fixed relative to the housing. The follower is prevented from moving from the first position toward the second position when the plunger element is in the first location, and the follower freed to move from the first position toward the second position when the plunger element moves from the first location to the second location such that the at least one biasing member shifts the follower from the first position to the second position to thereby move the shuttle for retracting the injection needle into the housing after injection.

In another form thereof, the present invention provides a delay mechanism for an automatic injection device having a housing and a syringe. The delay mechanism includes a shuttle for retracting the syringe in a first direction within the housing, a follower, means for moving the follower relative to the housing from a first position to a second position, the follower being configured to move the shuttle to retract the syringe in the first direction when the follower moves from the first position to the second position, means on the follower and the housing for guiding motion of the follower relative to the housing from the first position to the second position, a plunger adapted to force medication from the syringe, means to prevent the follower from being rotated from the first position toward the second position until the plunger has started to force medication from the syringe, and a means for damping rotational motion of the follower when the follower moves from the first position toward the second position.

One advantage of the present invention is that a delay mechanism may be provided which is compact in design.

Another advantage of the present invention is that a delay mechanism may be provided which allows for the secure retention after use of a retracted needle of an automatic injection device.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein:

FIGS. 13A, 13B and 13C are respectively perspective, first side and second side views of a housing center rod shown separate from the other device components;

Figure 1:
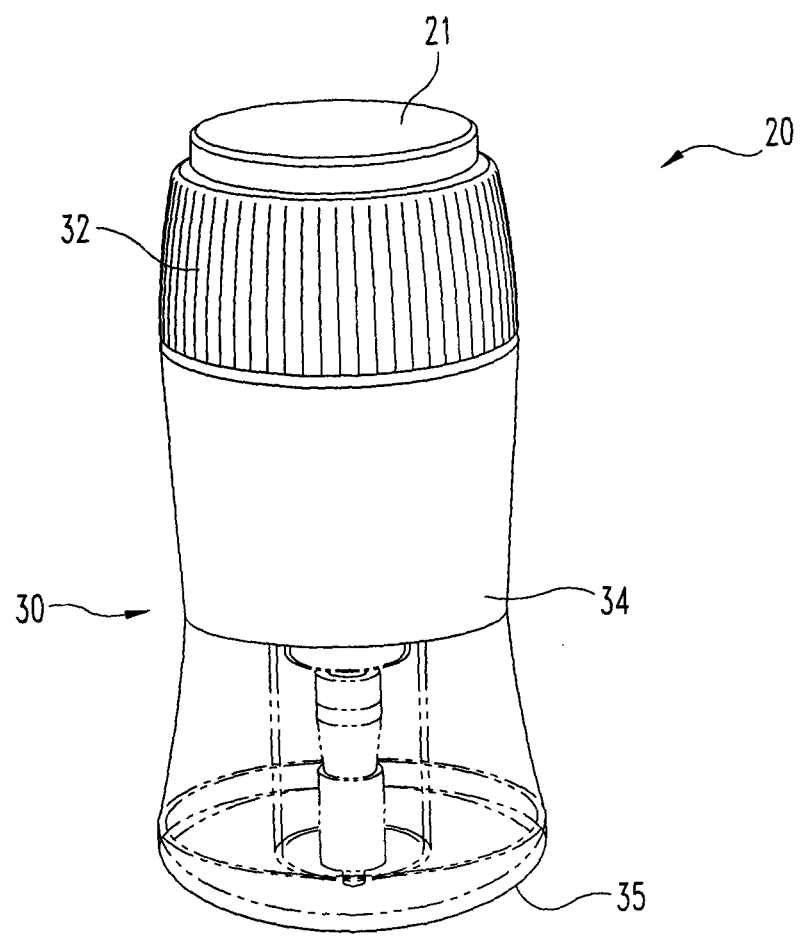
FIG. 1 is a perspective view of an automatic injection device with a delay mechanism of the present invention prior to its use.

Corresponding reference characters indicate corresponding parts throughout the several views. Although the drawings represent an embodiment of the present invention, the drawings are not necessarily to scale, and certain features may be exaggerated or omitted in some of the drawings in order to better illustrate and explain the present invention.

DETAILED DESCRIPTION OF THE INVENTION

Figure 2:
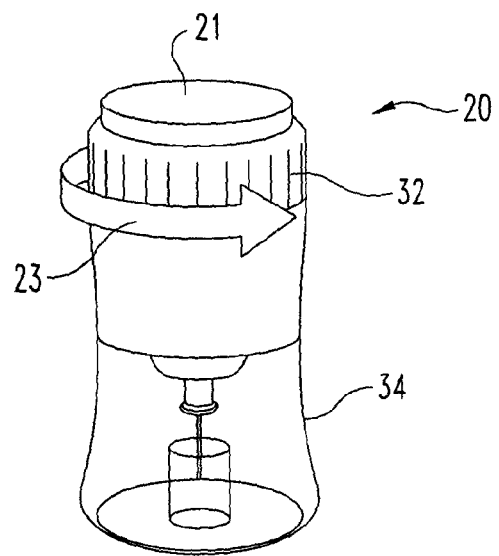
FIG. 2 is an abstract perspective view similar to FIG. 1, but wherein the needle cover is not shown and in which the abstractly shown needled syringe is more readily visible.
Figure 3:
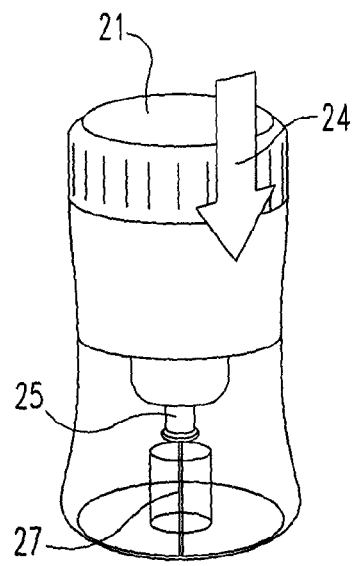
FIG. 3 is an abstract perspective view similar to FIG. 2, but after the device has been triggered, and at a time during use when the needle of the syringe extends from the device for penetrating a user.
Figure 4:
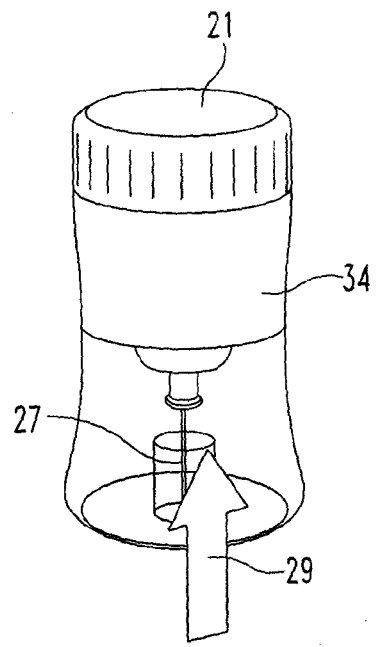
FIG. 4 is an abstract perspective view similar to FIG. 3, but after the device has completed the injection and retracted the needle of the syringe into the housing.

In FIG. 1, there is shown a perspective view of a first embodiment of an automatic injection device, generally designated 20, with a delay mechanism of the present invention. In FIGS. 2-4, device 20 is shown abstractly with a simple needled syringe, and with its needle cover, which during use is collapsed and pierced during an injection, not being shown. In FIG. 2, device 20 is shown being unlocked by rotating the safety sleeve 32 as indicated by arrow 23 about the housing main body 34 to an unlocked angular position. After device unlocking, and when the trigger button 21 is depressed as indicated by arrow 24, the needled syringe 25 of the device 20 is automatically driven downward such that the injection needle 27 of syringe 25 projects beyond the bottom end of the device housing to penetrate the user as shown in FIG. 3. The device then proceeds to inject automatically, that is without further user action, the medication contents of the syringe 25 through the needle 27, after which the syringe is retracted automatically, as indicated by arrow 29, such that the needle 27 is returned to within the housing as shown in FIG. 4. The inventive delay mechanism within device 20 helps to stage the operation to ensure that the medication contents are properly delivered prior to the needled syringe being retracted. The delay mechanism is also useful as a means of compensating for axial tolerances in the syringe and other device components.

Although the inventive delay mechanism is shown finding beneficial application in the device 20 described herein, such application is merely illustrative and not intended to be limiting. The inventive delay mechanism can be used in many differently configured automatic injection devices where its benefits are desired.

Figure 5:
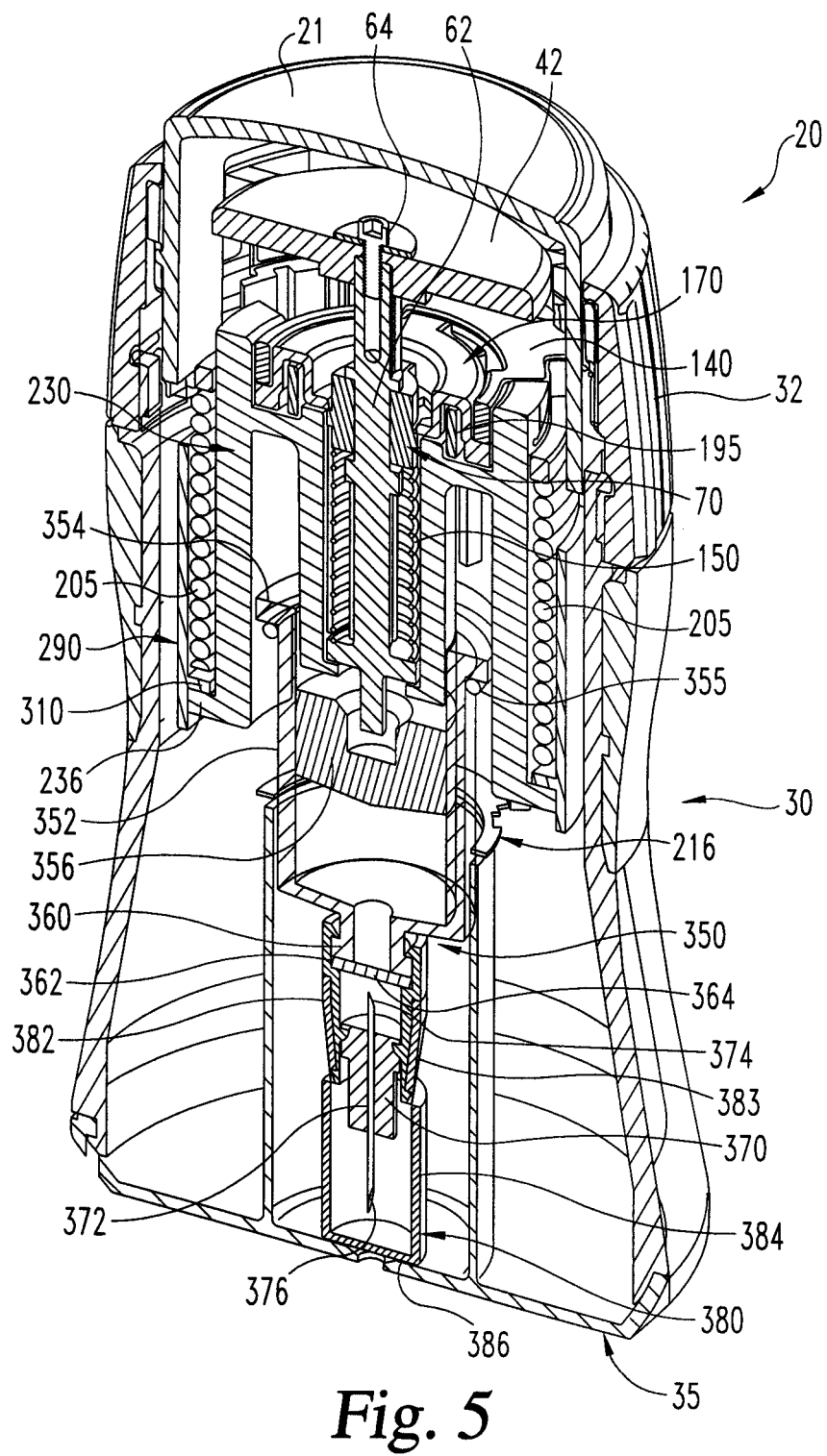
FIG. 5 is a longitudinal cross-sectional view of the automatic injection device of FIG. 1 prior to its unlocking and use.
Figure 6A:
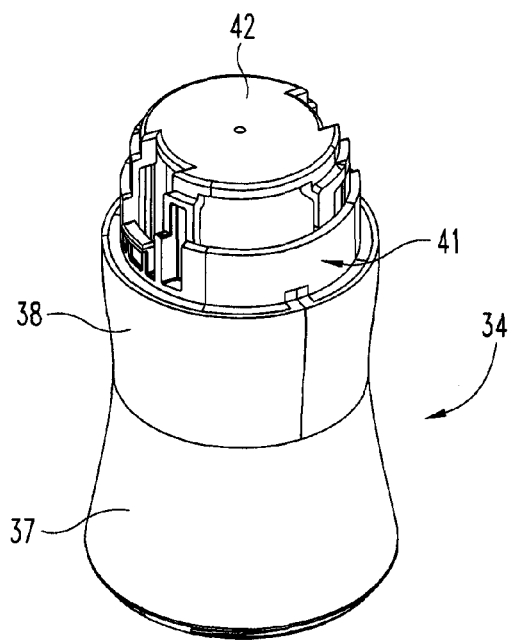
FIGS. 6A, 6B, 6C and 6D are respectively perspective, side, top and longitudinal cross-sectional views of a housing main body shown separate from the other components of the device of FIG. 1.
Figure 6B:
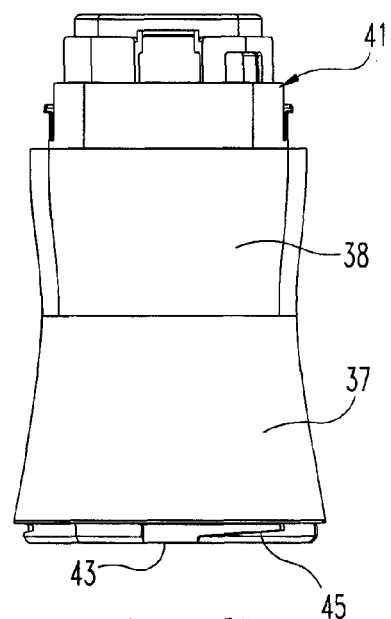
Figure 6C:
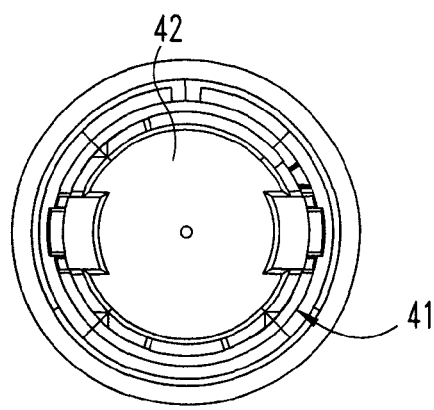
Figure 6D:
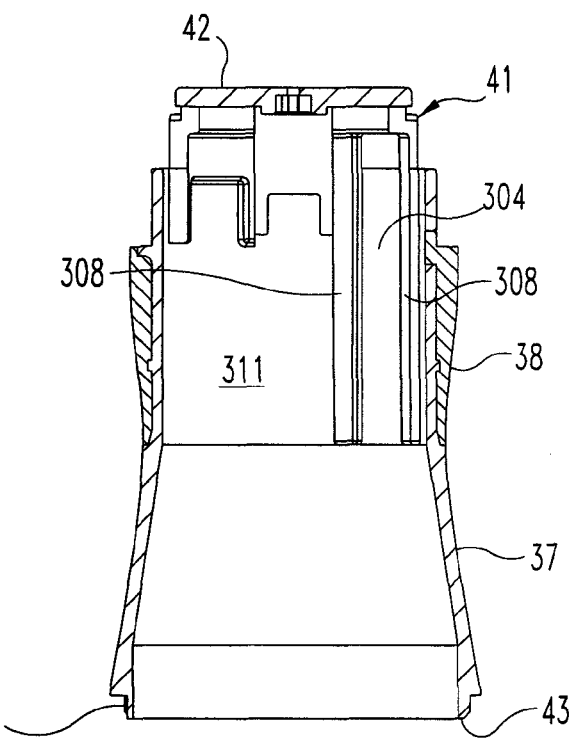
Figure 7A:
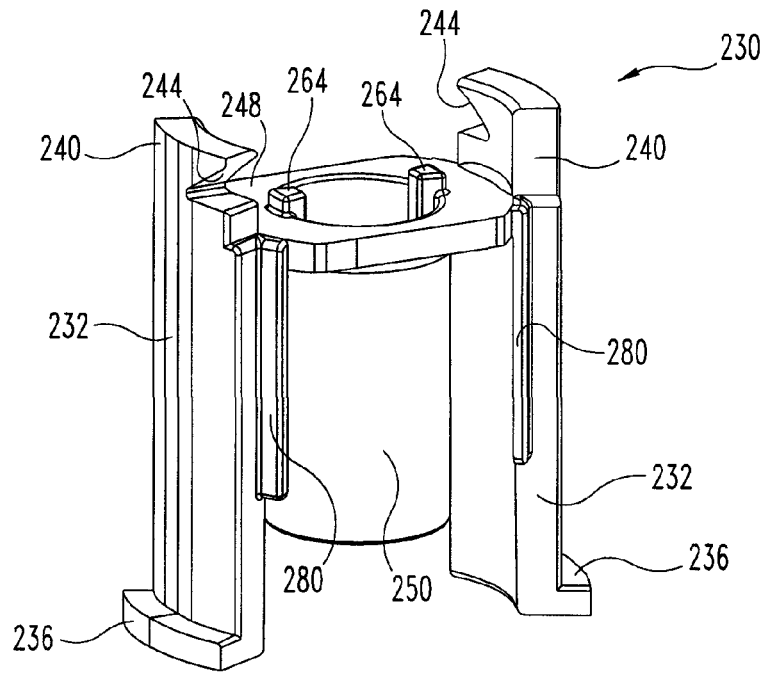
FIGS. 7A, 7B, 7C, 7D and 7E are respectively top perspective, bottom perspective, front, side and bottom views of a plunger element shown separate from the other device components.
Figure 7B:
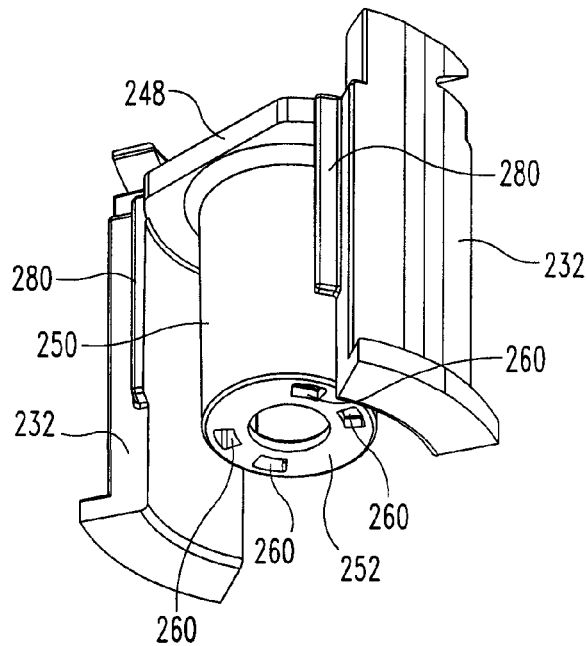
Figure 7C:
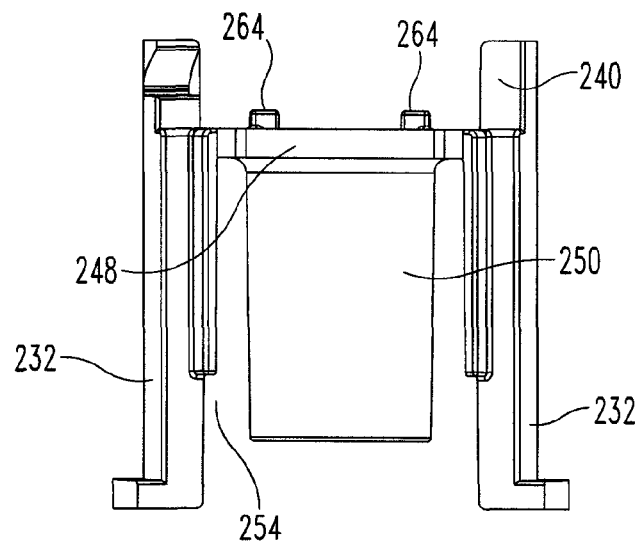
Figure 7D:
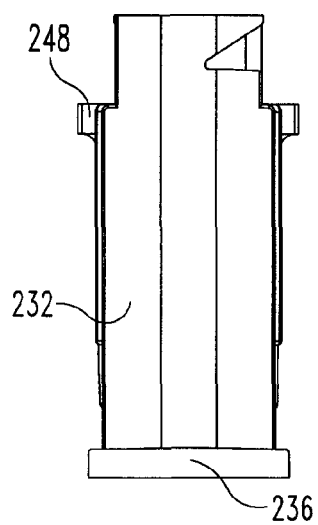
Figure 7E:
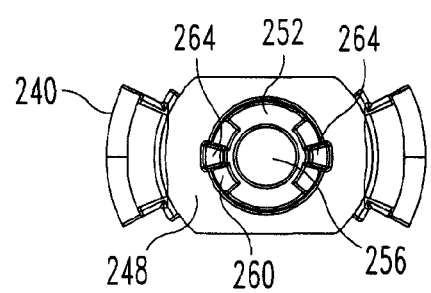

With reference again to FIG. 1 and to FIG. 5, device 20 includes an outer housing 30 in which are operationally disposed working components of the device. At the top or distal end of the housing and protruding axially therefrom is button 21. When safety sleeve 32 is rotatably oriented to unlock the button 21 that is then plunged by a user, or someone helping the user, the plunged button 21 allows rotation of a lock ring 140 within the housing and shown in FIG. 5 which disengages the plunger element 230 so as to trigger or start the automatic operative function of device 20. The safety sleeve 32 and trigger assembly for the device is further described in a provisional patent application filed with the United States Patent and Trademark Office on Mar. 14, 2013 as Application No. 61/782,929, and in an international patent application, with the same listed inventors as this case, filed with the United States Patent and Trademark Office as receiving office on the same date of this application and entitled "Trigger Assembly for an Automatic Injection Device", the entire disclosures of both those applications are hereby incorporated herein by reference.

As used herein, distal and proximal refer to axial locations relative to an injection site when the device is oriented for use at such site, whereby, for example, proximal end of the housing refers to the housing end that is closest to such injection site.

The axial height of housing 30 is formed by safety sleeve 32, a main body 34 and a base plate 35. Main body 34 is further shown in FIGS. 6A-6D. Main body 34 is formed from a two part molding process with a base portion 37 and an encircling sleeve portion 38. Base portion 37 is made of a transparent plastic material to allow visibility of the syringe contents, and sleeve portion 38 is made from an opaque plastic material. Above sleeve portion 38, the upper region, generally designated 41, of base portion 37 includes a disc portion 42 and is configured to mount safety sleeve 32 and button 21. A radially recessed bottom region 43 of main body 34 defines a central opening and is provided with external threading 45.

Figure 8A:
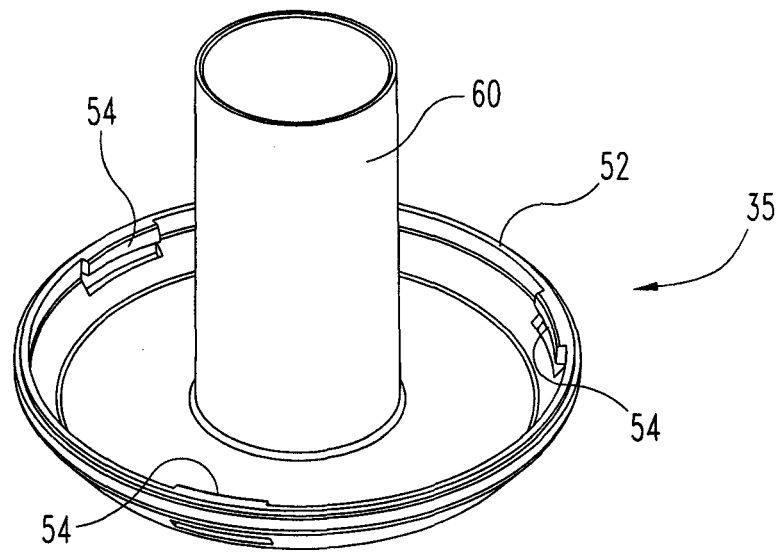
FIGS. 8A and 8B are respectively top perspective and longitudinal cross-sectional views of a housing base plate shown separate from the other device components.
Figure 8B:
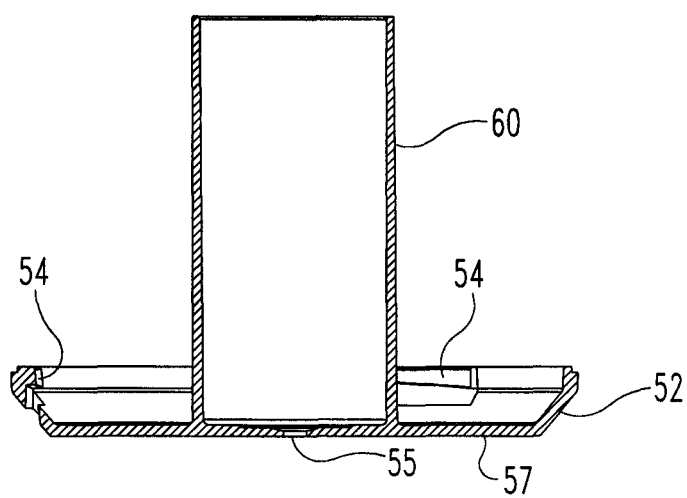
Figure 9A:
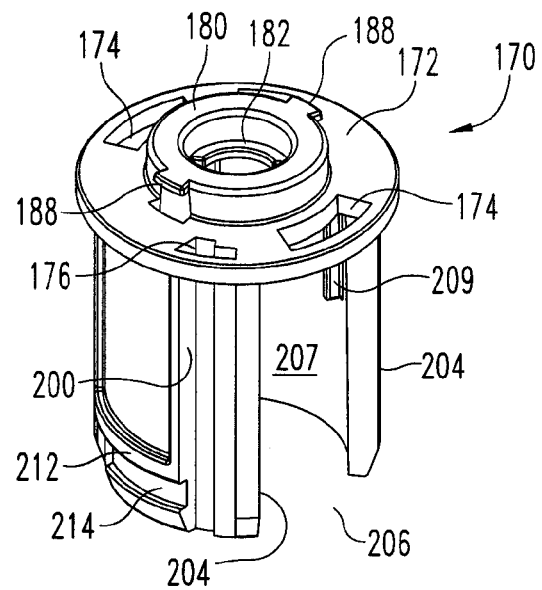
FIGS. 9A, 9B, 9C, 9D and 9E are respectively top perspective, first side, second side, longitudinal cross-sectional and top views of a shuttle member shown separate from the other device components.
Figure 9B:
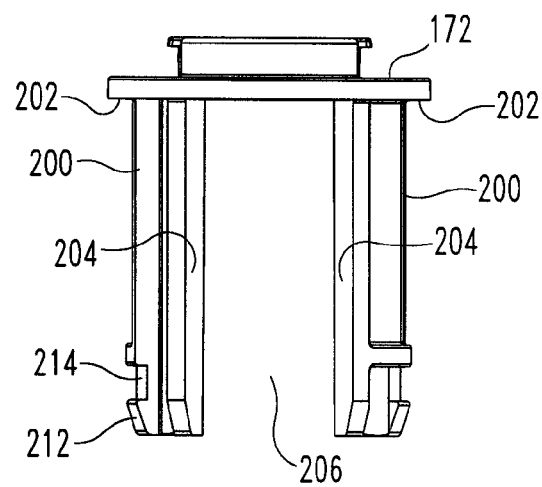
Figure 9C:
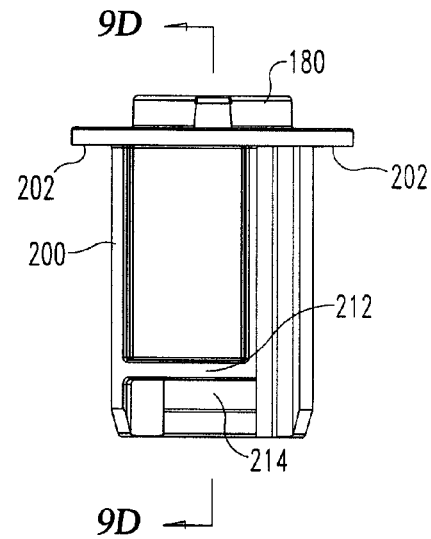
Figure 9D:
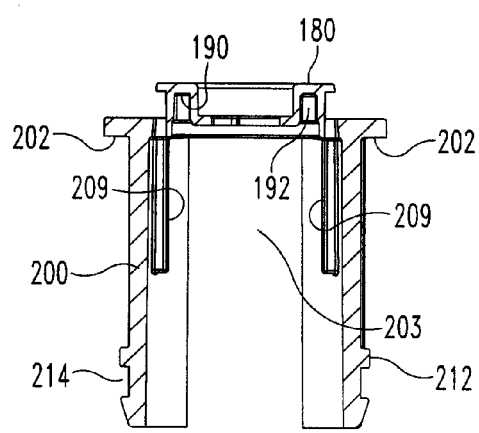
Figure 9E:
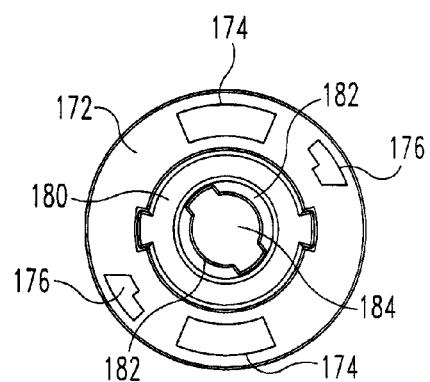
Figure 10A:
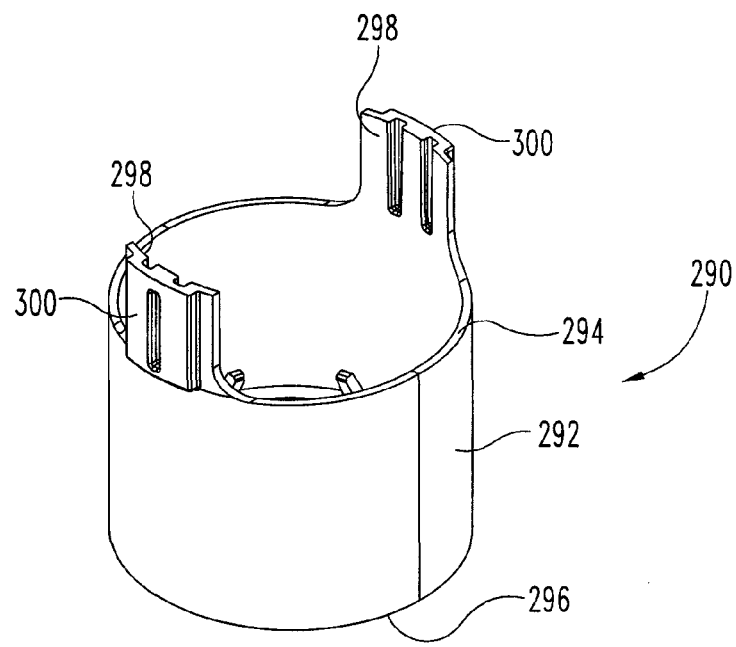
FIGS. 10A, 10B, 10C and 10D are respectively perspective, side, longitudinal cross sectional and top views of a syringe support member shown separate from the other device components.
Figure 10B:
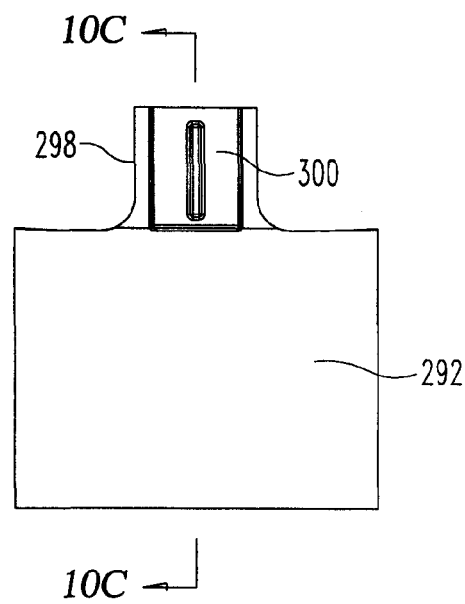
Figure 10C:
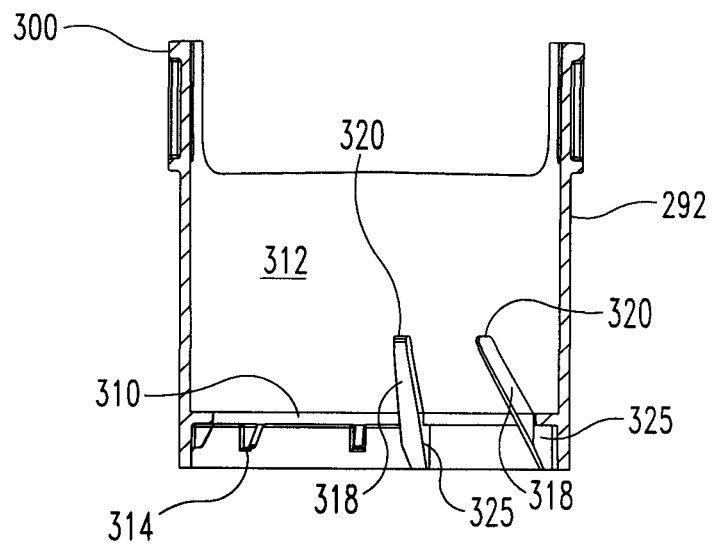
Figure 10D:
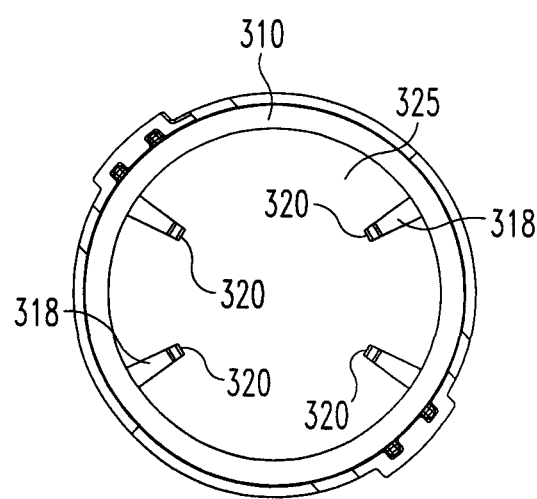

Housing base plate 35, further shown in FIGS. 8A and 8B, is made of the same transparent material as base portion 37.

The rim 52 of base plate 35 is threaded along its inner periphery at 54 that engages threading 45 to securely attach base plate 35 to main body 34. A positive locking detent feature between base plate 35 and body 34 may also be provided to ensure the base plate does not unscrew from the body. A small, central aperture 55 in the disc-shaped base 57 of base plate 35 through which a syringe needle moves out from and then back into the housing during use is ringed by a tube portion 60 that distally extends from base 57.

The housing also includes a central inner portion formed by a rod-shaped part or shaft 62 shown in FIG. 5 that depends from housing disc portion 42 in the center of main body 34. To facilitate manufacture and assembly, shaft 62 is separately formed and then fixedly secured, such as with a shown fastener 64 to be at all times rotatably and axially fixed relative to housing main body 34.

Housing shaft 62 supports a follower or delay element, generally designated 70, that is further shown in FIGS. 12A-12E. Delay element 70 is formed as one rigid piece and includes a central collar 72 having a pair of facing ribs or keys 74 that extend radially inward into an otherwise open center 76. Keys 74 extend the full axial height of collar 72. Two tabs or ears 78 project radially outward from diametric portions of collar 72 at the distal end of the collar. A ring-shaped damping fin 80 is concentric with collar 72. Fin 80 is connected to collar 72 by a spanning flange 82 that extends between the proximal end of fin 80 and the central axial region of collar 72. Although a single, continuous fin is provided, it could be replaced with differently shaped or numbers of fins in alternate embodiments.

Two holes 84 are provided through flange 82 centered one hundred eighty degrees apart to receive the upper ends of keys 264 of plunger element 230. Two openings 86 through fin 80 are provided directly radially outward of tabs 78 and angularly centered between the holes 84. Openings 86 are used during manufacture for molding of tabs 78, and also serve to allow damping fluid to move to opposite radial sides 81, 83 of fin 80.

A pair of legs 90 extends proximally from flange 82. Legs 90 are bowed in the angular direction to partially define a cylindrical hollow 91 below collar 72. The angular sides 92 of each leg 90 are made thicker for robustness and are angularly spaced from the opposing sides of the other leg 90 to provide axially extending openings 94 that are diametrically opposed.

Openings 94 serve as keyways for the plunger element keys 264 as their keyed engagement is used in the shown embodiment to maintain the follower 70 rotationally fixed relative to the housing shaft 62 to prevent, until such time as the plunger element 230 has moved axially a sufficient distance after triggering, the follower from moving toward another position, at which other position the syringe has been retracted. In alternate embodiments, the follower need not be keyed to the plunger element and can be otherwise prevented from moving along a track in the housing, which movement prevention is undone by the plunger element as it moves axially. For example, the follower could be directly connected to the housing, or a part rotatably fixed with the housing, such as the shuttle, via a latch or snap, or blocked from moving by a lock member that is rotatably fixed with but axially slidable relative to the housing. As the plunger element moves proximally, the plunger element unlatches or unsnaps the follower, or moves the lock member out of its position blocking the follower, such that the follower is then free to move on the housing track. Such alternate embodiments will be further understood in view of International Publications Nos. WO2011/109205 and WO2008/112472, the entire disclosures of which applications are hereby incorporated herein by reference.

Housing shaft 62 and delay element 70 are complementarily designed with keying to guide the movement of the delay element 70 both axially and rotatably relative to shaft 62. For this purpose and with reference to FIGS. 13A-13C, shaft 62 includes a generally cylindrical body 100 with a pair of recess or keyway regions 102 and a pair of recess or keyway regions 104 that are connected by axially extending channels 106, all of which closely accommodate keys 74. Regions 102 and 104 connected by channels 106 form tracks or keyways for the axially elongated keys 74. Only one such keyway is necessary, but two angularly spaced keyways balances the parts. Only one set of recess regions 102, 104 and channel 106 is visible in FIGS. 13B and 13C, but it will be appreciated that the sides of shaft 62 opposite to those sides shown in FIGS. 13B and 13C, other than with respect to disc section 132, are similar Each recess region 102 includes bottom shoulder 110 that extends the full angular span of that region, a top shoulder 112 that extends the full angular span other than where channel 106 opens into that region, an axially extending shoulder 114 that spans shoulders 110 and 112, and an end shoulder 116 that leads to channel 106. Each recess region 104 includes a top shoulder 120 that extends the full angular span of that region other than channel 122, a bottom shoulder 124 that extends the full angular span other than where channel 106 opens into that region, an end shoulder 126 continuing from channel 106, and a stop shoulder 128 that axially extends from bottom shoulder 124 to channel 122. Each of recess regions 102 are shown configured to produce strictly rotational motion of the follower 70, but each or both could be configured to produce an axial component of motion as well, meaning the follower moves both rotationally and axially while moving in recess regions 102.

Each top shoulder 120 may be provided with a not shown notch along a middle section of its angular extent, which notches serve as catches for holding the spring-loaded follower during an assembly step.

The shown tracks formed by recess regions 102 and axial channels 106 effectively produces a square jog in the tracks. During follower movement, when each key 74 moving along a recess region 102 reaches a position in the square jog of its respective track, the damped and slow rotation of the follower ends, and an undamped and rapid movement of follower 70 then occurs as key 74 shifts along channel 106 to recess region 102. This rapid movement provides a nearly instantaneous follower retraction and thereby makes the syringe retraction it achieves visibly, audibly and tactilely apparent to the user.

In an alternate embodiment, and to guide the follower as the follower moves from its rotationally locked position prior to device use to the position at which it has caused syringe retraction prior to being further moved to effect a locking of that retraction, the track may be formed to produce along all or part of its length a gradual helical sweep of the follower.

A grooved portion 130 of shaft 62 located proximally of recess regions 102 ends at a disc section 132, from which a stub 135 used in device assembly proximally extends. Disc section 132 includes an axially oriented opening 134 in which inserts an axially protruding proximal end or tip 152 of a biasing member 150.

Figure 14:
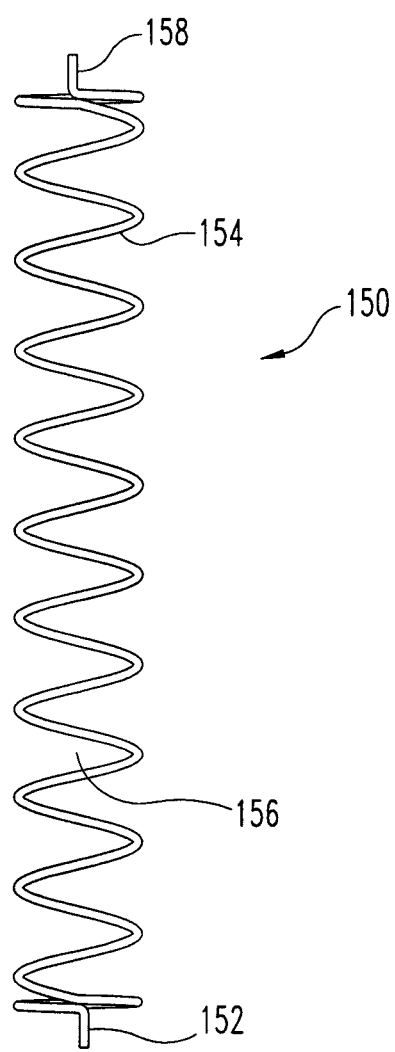
FIG. 14 is a side view of a spring for biasing the follower shown separate from the other device components.

Biasing member 150, shown best in FIG. 14, functions to bias follower 70 rotatably as well as axially relative to shaft 62. Biasing member 150 is shown as a cylindrical spring formed of a helically coiled wire 154. Spring 150 is selected to provide suitable torsional and axial forces within the available space, and the selection is dependent upon the device operation, such as the delay required, and the design of the cooperating components, such as the damping compound and follower and shuttle configurations. Other designs of biasing members, such as a metal or plastic flexure configured to perform the dual functions, may be substituted for the single metal coil spring shown. In alternate embodiments, and although the part count would increase, the single biasing member 150 may be replaced with two or more biasing members to serve the axial and rotational biasing functions, or may be replaced with an axial spring coupled with an additional piece, or driver, that provides the torsional preload via a cam or thread surface.

The internal opening 156 of spring 150 freely receives shaft 62, while the outer diameter of spring 150 freely fits within cylindrical hollow 91 of follower 70. The axially extending distal tip 158 of spring 150 inserts within a not shown blind pocket formed in the underside of collar 72. The opposite end coils of spring 150 act against the underside of collar 72 and the distal face of shaft disc section 132. Spring 150 is symmetric such that ends 158 and 152 are interchangeable.

A shuttle member, generally designated 170, is axially held by delay member 70 within the device housing 30. Shuttle member 170, which is further shown in FIGS. 9A-9E, cooperates with a shuttle clip element 216 to form a shuttle for syringe retraction. Shuttle member 170 is molded in one piece and includes an annular plate portion 172 that includes a pair of diametrically disposed arcuate slots 174 for receiving the plunger element 230 and a pair of diametrically disposed openings 176 used in device manufacturing assembly. At the center of plate portion 172 is an upstanding collar 180 which rings a center portion 182 that is recessed proximally from the distal face of collar 180. Center portion 182 defines a keyed opening 184 shaped to receive therethrough the inserted distal end of follower collar 72 and tabs 78 during manufacturing assembly. During such assembly, rotation of the inserted collar 72 results in center portion 182 being captured between collar tabs 78 and spanning flange 82 such that shuttle member 170 is axially fixed relative to follower 70 throughout device operation. A pair of diametrically opposed tabs 188 project radially outward from collar 180 and serve to locate lock ring 140 axially relative to shuttle member 170.

The U-shaped underside 190 of collar 180 defines an annular hollow or pocket 192 and provides a support surface for damping fluid as follower 70 rotates relative to the shuttle member 170.

A damping compound or fluid indicated as 195 in FIG. 5, such as a silicone grease thickened with Teflon available from Nye Lubricants as Nye fluorocarbon gel 880, fills annular pocket 192. Follower fin 80 fits within hollow 192 such that damping compound 195 is disposed both radially inward and outward of the fin, resulting in a damping or delay effect as the follower fin 80 tries to rotate relative to the collar underside 190 with the viscous damping fluid providing a resistance to this rotation during operation. Other compounds with different properties may be selected by one of skill in the art.

Furthermore, the positioning of the fluid filled pocket and the fin that inserts therein on the shuttle member and follower respectively may be switched to the follower and shuttle member respectively in an alternate embodiment.

Shuttle member 170 further includes two legs 200 that are bowed in the radial direction and which proximally extend from annular plate portion 172. Legs 200 are spaced from the outer radial periphery of plate portion 172 such that an overhanging region 202 of plate portion 172 provides an annular surface against which the distal end of a plunger biasing spring 205 directly abuts. A pair of not shown, diametrically opposed, depending hooks may be provided on the outer radial periphery of plate portion 172 to ensure spring 205 remains centered on the shuttle member 170. The axially extending, angular sides 204 of each leg 200 are angularly spaced from the opposing sides of the other leg 200 to provide axially extending and diametrically opposed openings 206 in which interfit the plunger element legs 232 to rotatably fix the plunger element 230 relative to the shuttle member 170. Legs 200 are bowed in the radial direction to partially define a cylindrical hollow 203. The inner radial surfaces 207 of legs 200 include longitudinally extending ribs 209 that serve as stops to prevent the syringe from moving upward within shuttle member 170.

Figure 11A:
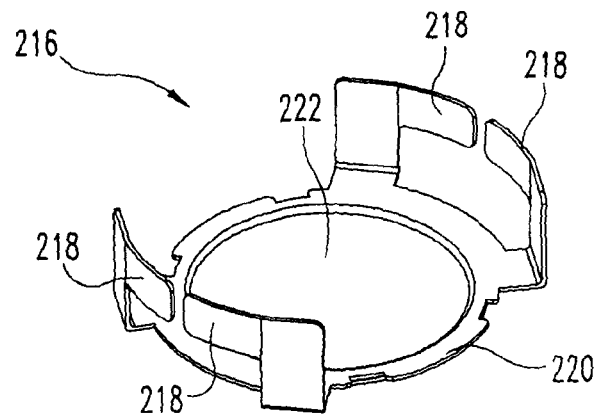
FIGS. 11A and 11B are respectively perspective and top views of a shuttle clip element shown separate from the other device components.
Figure 11B:
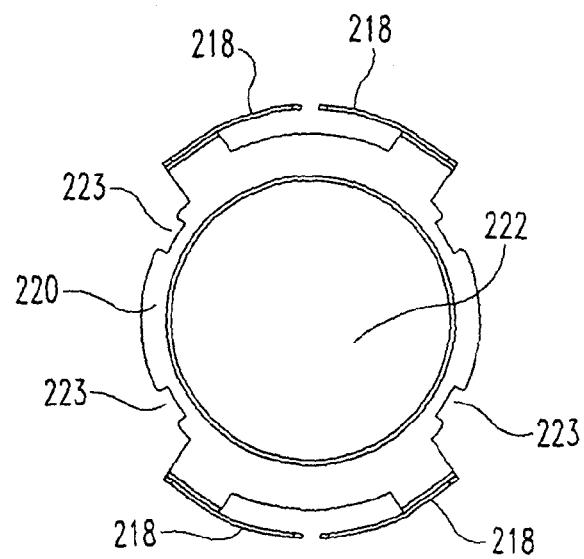
Figure 12A:
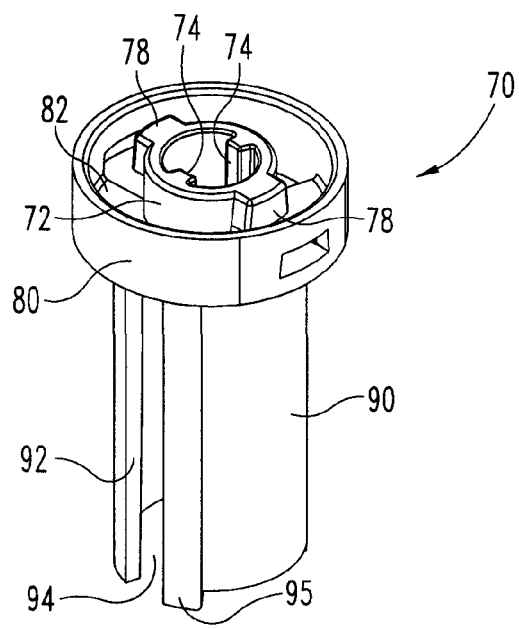
FIGS. 12A, 12B, 12C, 12D and 12E are respectively perspective, first side, second side, first longitudinal cross sectional and second longitudinal cross sectional views of a delaying element or follower shown separate from the other device components.
Figure 12B:
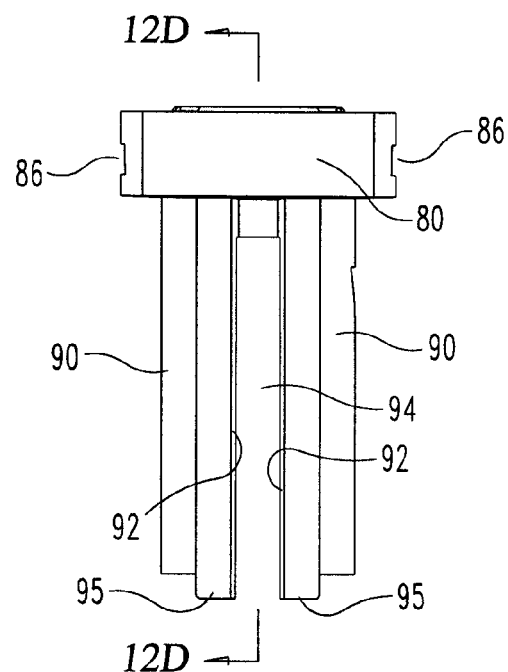
Figure 12C:
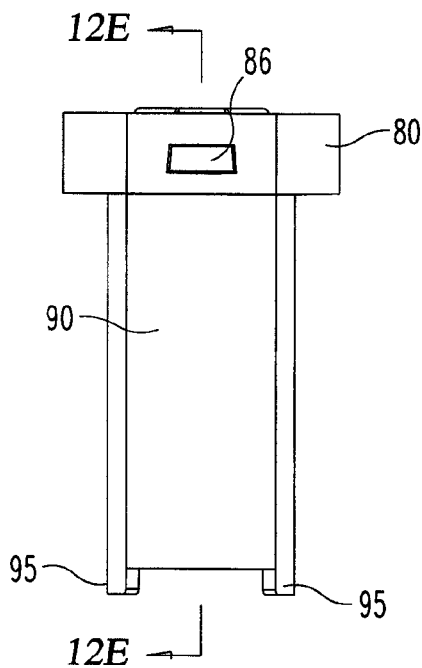
Figure 12D:
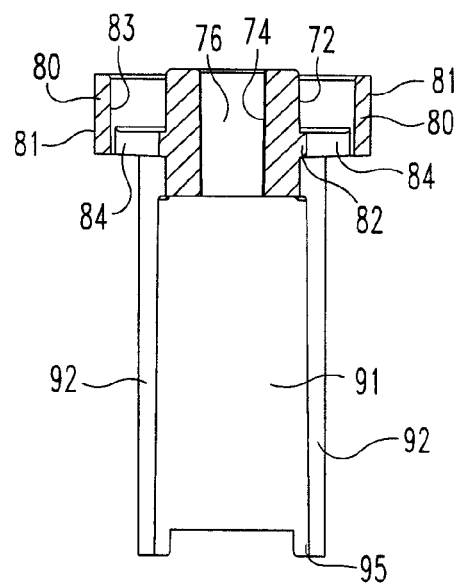
Figure 12E:
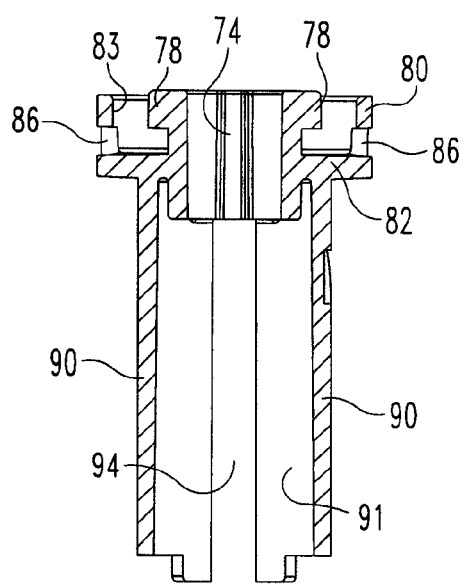

The lower regions of the outer radial periphery 212 of legs 200 are recessed at 214 to accommodate resilient flanges 218 of a clip element, generally designated 216, that is further shown in FIGS. 11A and 11B. Clip element 216 is made of a single piece of stainless steel. Flanges 218 resiliently grip legs 200 to fixedly secure the clip element 216 with the shuttle member 170 so that they act as a single part. Flanges 218 extend to a ring-shaped base 220 having a central opening 222. Opening 222 is sized to allow the syringe barrel 352, but not distal flange 354, to fit therethrough. Ring-shaped base 220 is sized to engage syringe flange 354 and designed to stay axially clear of the top of tube portion 60. Notches 223 in base 220 allow passage of sleeve arms 318 described further below.

A plunger element that during use is axially shifted within housing 30 to drive both needle insertion and medication delivery is generally indicated at 230 and further shown in FIGS. 7A-7E. Plunger element 230 includes axially extending legs 232 with outward directed flanged ends 236 at the proximal ends of the legs. The upper regions 240 of legs 232 above plate portion 248 are sized and shaped to insert within slots 174 of shuttle plate portion 172. Upper regions 240 include cam faces 244 that engage complementary portions of the lock ring 140. Until the trigger assembly of device 20 is activated by the user to disengage the lock ring portions from cam faces 244, plunger element 230 is effectively latched and prevented from axially moving proximally under the biasing force of compressed spring 205.

Plunger element 230 also includes a central plate portion 248 that spans legs 232. A cylindrical tube 250 with a partially closed bottom end 252 depends from plate portion 248 between plunger legs 232. Bottom end 252 directly engages the sealing piston or plunger 356 of the device syringe 350. Tube 250 is sized with a transverse cross-section that allows its insertion into barrel 352 of syringe 350. A radial gap 254 between the outer radial periphery of tube 250 and the inner radial periphery of legs 232 is sized to receive the upper extent, in the shown case the flange 354 and adjacent barrel 352, of syringe 350 when the plunger element tube 250 inserts into the syringe barrel 352. The hollow interior 256 of tube 250 is sized to house follower legs 90 therein until device operation. Four openings 260 in end 252 provide clearance in which initially fit the extending tabs or extensions 95 on follower legs 90, which extensions are to keep the follower 70 and shuttle element 230 engaged for a longer portion of the axial travel of the plunger element. The upper region of hollow interior 256 is interrupted by a pair of inwardly projecting keys 264. Keys 264 fit within openings 94 of follower 70 to prevent the follower 70 from rotating relative to plunger element 230 until the keys 264 drop below openings 94 when the plunger element 230 is moved during an injection such that the follower 70, relative to the plunger element 230, rises out from within tube 250. Keys 264 extend above plate portion 248 to fit into clearance holes 84 of follower 70. Keys 264 extend above plate portion 248 to keep the follower 70 and shuttle element 230 engaged for a longer portion of the axial travel of the plunger element.

Plunger element 230 is rotatably keyed with shuttle member 170 at all times within device 20 due to the interfitting of plunger element legs 232 with shuttle member legs 200. Projecting rib portions 280 are the portions of legs 232 that engage plunger leg sides 204. Rib portions 280 are radially reduced for the sleeve arms 318 to pass over during device assembly.

Plunger element 230 is surrounded along most of its axial length by a syringe support member, generally designated 290, that is further shown in FIGS. 10A-10D. Syringe support member 290 includes a tubular body or sleeve 292 extending from a distal end 294 to a proximal end 296. A pair of diametrically opposed flanges 298 projecting from distal end 294 each include a radially outwardly projecting key 300 that slide axially within diametrically arranged channels or keyways 304 provided on housing main body 34 via vertically extending ribs 308 formed on the interior surface 311 of base portion 37.

Sleeve 292 includes a spring-supporting shelf 310 provided on the interior surface 312 near proximal end 296. Shelf 310 is buttressed by a series of angularly spaced gussets 314 along the underside of shelf 310. Two diametrically arranged pairs of support arms 318 upwardly project at an angle from interior surface 312 below shelf 310. The flattened upper tips 320 of arms 318 are spaced within the hollow 325 of sleeve 292 to engage the underside of flange 354 of syringe barrel 352. Arms 318 serve to hold the syringe 350 within the housing 30 prior to the device being used.

The end coil of spring 205 that drives medication injection abuts the top face of shelf 310. As best shown in FIG. 5, spring 205 acts against the plunger element ends 236 via the interposed shelf 310. Flanged ends 236 of plunger element 230 nest between the lower ends 325 of arms 318 such that the plunger element 230 is rotatably fixed with syringe support member 290 and thereby device housing 30. This operative connection means that syringe support member 290 acts as a part of the drive plunger of device 20 with plunger element 230. The medication filled, needled syringe for use with the inventive delay mechanism of the present invention 290 may be one of a variety of syringe designs, such as a staked needle syringe that would generally have a configuration as shown in FIGS. 2-4. Different needle covers could also be employed. Device 20 is shown in FIG. 5 as having a needle syringe, generally designated 350 with a needle cover 380. Syringe 350 and cover 380 will be further understood in view of a conceptually similar syringe design described in International application no. PCT/US2012/051702, the entire disclosure of which application is hereby incorporated herein by reference.

Needle syringe 350 includes a barrel 352 with a radially outwardly extending, circumferential rib or flange 354 at its distal end. An elastomieric ring 355 under flange 354 cushions impact of flange 354 on shuttle base 220. An elastomeric piston 356 slidably seals with the barrel interior to prevent the medication contents from exiting the top end of barrel 352. A collar portion 360 at the proximal end of barrel 352 connects with a hub 362 that has a resilient portion that forms a pierceable septum 364 that seals the bottom of the medication reservoir.

A needle carrier 370 holds a double-ended cannula 372. Needle carrier 370 is axially movable in a keyed or rotatably fixed fashion within hub 362 between detented axial positions. Needle carrier 370 is shown abstractly in FIG. 5, but is further shown in FIGS. 15-17 as having resilient arms with detents on their upper ends that engage nubs provided in the interior surface of hub 362. Distal tip 374 of cannula 372 is for piercing septum 364 and cannula proximal tip 376 is for piercing cover 380 and penetrating a user.

Needle cover 380 maintains the sterility of cannula 372 prior to device use and is made of a single air-tight elastomeric piece. Cover 380 includes ring portion 382 that mounts to hub 362 and a hinging region 383 at the upper end of a collapsing body 384 with a needle penetrable end region 386.

Figure 15:
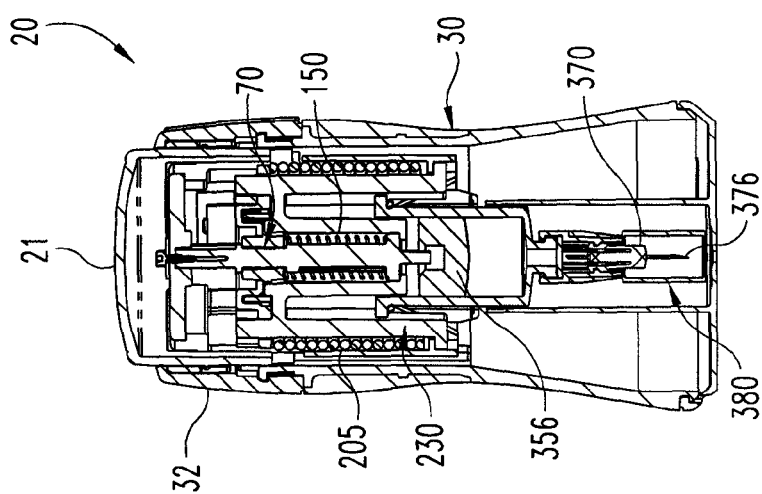
FIG. 15 is a longitudinal cross-sectional view of the device of FIG. 1 shown prior to being unlocked for use.

The construction of device 20 will be further understood in view of a description of its operation. The device is initially configured as shown in FIG. 5 and FIG. 15, with spring 205 under compressive preloading to acting to provide a biasing force on plunger 230 relative to shuttle member 170. Despite this biasing force, plunger 230 can not move axially proximally relative to the shuttle as it is effectively latched with the lock ring 140 mounted to shuttle member 170. Spring 150 is under a torsional preloading and an axial preloading each tending to bias follower 70 relative to the housing 30 and more particularly shaft 62. Despite this biasing, follower 70 can not move distally within the housing as the interfitting of follower keys 74 within recess regions 102 results in keys 74 abutting top shoulders 112, and the keying of follower 70 with plunger element 230 by keys 264 fitting within openings 94 of follower 70 prevents rotation of the follower within the housing. Follower 70, and the held shuttle member 170, can not move proximally as follower keys 74 abut shaft shoulders 110. To allow for an injection, safety sleeve 32 is manually rotated by a user, or someone helping the user, to unlock button 21 and the device 20 is placed on an injection site. When the trigger assembly is then operated by depressing button 21, plunger element 250 is released to be shifted by spring 205 proximally within the housing.

Plunger element 250, due to the direct engagement of the bottom end 252 of its tube 250 with syringe plunger 356, drives plunger 356 proximally which initially moves barrel 352 downward to cause cannula tip 384 to pierce cover region 386 and extend through base plate opening 55 to penetrate the user's skin. Cover 380 begins to axially collapse when the barrel 352 moves downward. Cannuala tip 374 has yet to pierce septum 364 as it is still axially retained within hub 360.

As the plunger element 230 is continued to be shifted downward by spring 205, syringe barrel 352 is continued to be driven proximally, with cover 380 continuing to collapse. When needle carrier 370 abuts housing base 57, with the cover region 386 sandwiched therebetween, it can travel no further proximally, and further proximal motion of barrel 352 causes the hub 360 to move downward relative to the needle carrier 370 such that septum 364 is pierced by needle tip 374.

Further downward advancement of plunger element 230 continues to move barrel 352 proximally until barrel flange 354, cushioned by ring 355, abuts clip element base 220, at which point the barrel 352 can not move proximally, the cover 380 is fully collapsed, and further proximal motion of plunger element 230 drives plunger 365 further downward within barrel 352 as tube 250 inserts farther into barrel 352, causing the syringe contents to be forced through cannula 372 and into the user.

Figure 16:
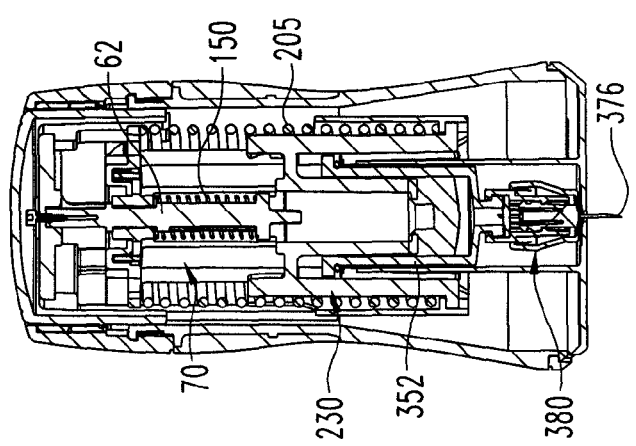
FIG. 16 is a longitudinal cross-sectional view of the device of FIG. 14 at the stage of operation when the follower is rotationally unlocked from the plunger element.
Figure 17:
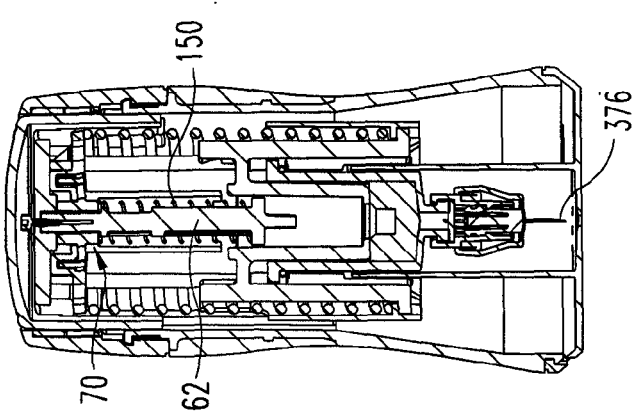
FIG. 17 is a longitudinal cross-sectional view of the device of FIG. 14 after use is completed with its syringe needle being locked securely in the retracted position.

As plunger element 230 moves proximally under bias of spring 205, keys 264 slide down follower legs 90 within openings 94 until clearing tips 95, at which point the follower 70 is rotationally unlocked from the plunger element 230. This unlocking typically will be designed to occur shortly before the end of proximal travel of the plunger, but can be earlier depending on the designed for delaying effect of the delay mechanism. FIG. 16 illustrates device 20 at this point of operation.

When rotationally unlocked, follower 70, as urged by the torsional preloading of biasing member 150, starts to rotate around shaft 62 with keys 74 sliding angularly within recess regions 102. This follower rotation is also relative to shuttle member 170 that remains rotationally fixed within the housing via its keyed relationship to plunger element 230. The viscous damping compound 195 between follower fin 80 and shuttle collar 180 dampens or offers a resisting force to this follower rotation, which resistance results in a passage of time before the follower shifts distally as described below, during which time remaining medication can be properly expelled from the syringe through the needle tip 376.

Rotation of follower 70 about shaft 62 as driven by spring 150 continues until follower keys 74 abut end shoulders 116, at which point keys 74 are aligned with channels 106. By then, plunger element 230 has completed its proximal travel to fully move syringe plunger 356 into syringe barrel 112 to expel a suitable dose, and under the axial force provided by spring 150, follower 70 is then driven distally within housing 30 such that keys 74 slide through channels 106 and into recess regions 104 until abutting top shoulders 120. This distal motion of follower 70 simultaneously and identically moves the shuttle member 170, and the shuttle clip element 216, distally. As clip element 216 so moves, and due to its engagement of clip base 220 with the underside of flange 354, syringe 350 is carried by the shuttle distally so as to retract the proximal 376 of the injection needle 372 to a protected position within the housing 30.

After needle retraction, a further follower rotation produces a locking of the retracted needle. In particular, when keys 74 abut shoulders 120, keys 74 are disposed within recess regions 104. The torsional preloading of biasing member 150 still remaining restarts the rotation of follower 70 in the same angular direction around shaft 62, with keys 74 sliding angularly within recess regions 104. When keys 74 abut stop shoulders 128, the follower rotation is halted. If top shoulders 120 are notched to provide follower catch features as described above, follower rotation is instead halted when keys 74 slip into these notches. Keys 74 do not continue into channels 122, which channels are used during assembly of the follower 70 to shaft 62, as during assembly of shaft 62 to housing disc portion 42 the fastener 64 effectively makes channel 122 impassable to the keys 74. Because follower 70, and therefore the shuttle including shuttle member 170, then can not be shifted proximally due to the abutting engagement of shoulders 124 by keys 74, the needled syringe 350 is locked in a retracted position. At this point, device 20 is configured as in FIG. 17, and the user then can dispose or otherwise handle the device in the normal course.

While this invention has been shown and described as having preferred designs, the present invention may be modified within the spirit and scope of this disclosure. For example, the inventive delay mechanism can have differently shaped parts or can be used in devices with different other components, such as alternate triggers. Furthermore, the manner in which the various parts are keyed together, and the fact that certain parts are keyed directly to other parts, may be changed in alternate embodiments. For example, the keys and keyways on various parts may by switched, or the shuttle could be directly keyed with the housing to be rotatably fixed rather than indirectly keyed, such as through the plunger element. Still further, and while the described plunger element drives both syringe advancement as well as advancement of the syringe piston within the barrel, the delay mechanism could be employed in a device in which the plunger element that it engages merely drives piston advancement within the barrel. Still further, while the damping compound is provided directly between the shuttle and the follower in the shown embodiment, in alternate embodiments, and instead of or in addition to such follower and shuttle direct damping feature, the damping feature can be provided between the follower and the housing directly, though such may delay the axial movement of the follower relative to the housing and thereby slow syringe axial retraction. This application is therefore intended to cover any variations, uses or adaptations of the invention using its general principles. Further, this application is intended to cover such departures from the present disclosure as come within known or customary practice in the art to which this invention pertains.

We claim:

1. In an automatic injection device including a housing and a medication filled syringe having a barrel, a piston, and an injection needle, the device operable for moving the syringe in a first direction relative to the housing to extend the injection needle beyond the housing, a delay mechanism comprising:
    a shuttle rotatably fixed relative to the housing and configured for engaging the syringe for retraction;
    a one-piece follower adapted for shifting said shuttle in a direction opposite to the first direction, said follower keyed with the housing for movement from a first position on the housing to a second position on the housing, said second position axially spaced from said first position in said direction opposite to the first direction, said second position rotationally spaced from said first position;
    a damping compound between surfaces of said follower and at least one of said shuttle and the housing to dampen rotation of said follower;
    at least one biasing member providing a force urging said follower from said first position to said second position;
    a biased plunger element adapted to drive the piston within the barrel to force medication through the injection needle for an injection, said biased plunger element biased in the first direction within the housing from a first location to a second location, said plunger element rotatably fixed relative to the housing; and
    said follower prevented from moving from said first position toward said second position when said plunger element is in said first location, said follower freed to move from said first position toward said second position when said plunger element moves from said first location to said second location such that said at least one biasing member shifts said follower from said first position to said second position to thereby move said shuttle for retracting the injection needle into the housing after injection.

2. The delay mechanism of claim 1 wherein said follower includes a collar through which axially extends a rod of the housing.

3. The delay mechanism of claim 2 wherein said collar includes at least one key that fits within at least one keyway on said rod, wherein said at least one keyway guides said follower to move strictly rotationally relative to said rod and then strictly in the direction opposite to the first direction along said rod when said follower moves from said first position to said second position.

4. The delay mechanism of claim 3 wherein said at least one key of said collar includes a pair of diametrically opposed keys, and wherein said at least one keyway includes a pair of recess regions with channels extending therefrom on opposite sides of said rod.

5. The delay mechanism of claim 1 wherein said follower is keyed with said plunger element when said plunger element is in said first location to prevent relative rotational motion, said follower being unkeyed from said plunger element to allow relative rotational motion when said plunger element moves from said first location to said second location.

6. The delay mechanism of claim 5 wherein said plunger element includes at least one key that fits within at least one keyway of said follower to engage said follower and said plunger element when said plunger element is in said first location to prevent relative rotational motion.

7. The delay mechanism of claim 1 wherein said plunger element includes a tube portion shaped to fit within the syringe barrel, wherein at least a portion of said follower fits within an interior hollow of said tube portion.

8. The delay mechanism of claim 7 wherein said follower is keyed with said plunger element when said plunger element is in said first location to prevent relative rotational motion, said follower being unkeyed from said plunger element to allow relative rotational motion when said plunger element moves from said first location to said second location, said plunger element including at least one key that fits within at least one keyway of said follower to engage said follower and said plunger element when said plunger element is in said first location to prevent relative rotational motion.

9. The delay mechanism of claim 8 wherein at least a portion of said follower that fits within said interior hollow comprises legs defining said at least one keyway of said follower, said at least one key of said plunger element protruding into said interior hollow.

10. The delay mechanism of claim 1 wherein said at least one biasing member acts directly between a center rod of the housing and said follower.

11. The delay mechanism of claim 1 wherein said shuttle comprises a collar with an annular pocket that opens in the first direction, wherein said follower comprises at least one fin that fits within said pocket, and wherein said damping compound is disposed within said pocket between said collar and said at least one fin.

12. The delay mechanism of claim 11 wherein said fin consists of a single, continuous ring-shaped member.

13. The delay mechanism of claim 1 wherein said shuttle comprises a surface against which directly acts a biasing element that biases said plunger element in the first direction within the housing, said follower disposed radially inward of said shuttle surface.

14. The delay mechanism of claim 13 wherein said biasing element is a coiled spring and said follower includes legs that fit within said coiled spring.

15. The delay mechanism of claim 1 wherein said follower is further keyed with the housing for movement from said second position on the housing to a third position on the housing, said third position rotationally spaced from said second position, said follower cooperatively configured with the housing at said third position to prevent movement of said follower in the first direction, whereby the injection needle retracted into the housing is axially locked from moving in the first direction.

16. The delay mechanism of claim 15 wherein said third position is rotationally spaced from said first position.

17. The delay mechanism of claim 16 wherein said at least one biasing member provides a torsional force to move said follower from said second position to said third position.

18. The delay mechanism of claim 1 wherein said plunger element and said shuttle each include angularly spaced legs, said legs of said plunger element and said legs of said shuttle interfitting to rotationally lock together said plunger element and said shuttle while permitting axially motion therebetween.

19. The delay mechanism of claim 18 wherein each of said follower, said shuttle and said plunger element include axially extending legs, wherein said legs of said follower are concentrically disposed around a rod of the housing, and wherein said legs of said shuttle element and said legs of said plunger element are concentrically disposed around said follower.

20. The delay mechanism of claim 19 wherein a coiled spring that biases said plunger element in the first direction is concentrically disposed around all of said rod of the housing, said legs of said follower, and said legs of said shuttle element and said legs of said plunger element.

* * * * *